US008986296B2

(12) United States Patent
Peyman

(10) Patent No.: US 8,986,296 B2
(45) Date of Patent: Mar. 24, 2015

(54) SYSTEM AND METHOD FOR GENERATING HEAT AT TARGET AREA OF PATIENT'S BODY

(71) Applicant: Nazmi Peyman, Richmond, VA (US)

(72) Inventor: Nazmi Peyman, Richmond, VA (US)

( * ) Notice: Subject to any disclaimer, the term of this patent is extended or adjusted under 35 U.S.C. 154(b) by 0 days.

(21) Appl. No.: 14/269,451

(22) Filed: May 5, 2014

(65) Prior Publication Data

US 2014/0236139 A1     Aug. 21, 2014

(51) Int. Cl.
*A61B 18/18* (2006.01)
*A61N 1/40* (2006.01)
*A61B 18/00* (2006.01)
*A61N 5/02* (2006.01)

(52) U.S. Cl.
CPC ............... *A61B 18/18* (2013.01); *A61N 1/406* (2013.01); *A61B 2018/00791* (2013.01); *A61N 5/025* (2013.01)
USPC .............................................. 606/33; 606/41

(58) Field of Classification Search
USPC .................................................... 606/32–45
See application file for complete search history.

(56) References Cited

U.S. PATENT DOCUMENTS

2011/0224665 A1* 9/2011 Crosby et al. ................... 606/33
2013/0274735 A1* 10/2013 Hastings et al. ................ 606/34

* cited by examiner

*Primary Examiner* — Jospeh Stoklosa
*Assistant Examiner* — Amanda Scott
(74) *Attorney, Agent, or Firm* — Barry Choobin; Patent 360 LLC

(57) ABSTRACT

The embodiments herein provide a method and system for generating heat at a target area of a patient's body for treatment of lesions, tumors, cancer cells, body pain and nerve pain. The heat generated inside a target tissue is distributed throughout the target area. The system and method provides a real time monitoring of the generated heat and the temperature of the tissue. The system comprises a radio frequency (RF) antenna/transducer for receiving the generated RF waves from the RF generator. A controller/optimizer is provided for controlling a frequency of the RF waves and a transmission timing of the RF waves. A RF absorber/distributor comprising a plurality of closed loop circuits is provided. A miniaturized thermometer is arranged inside the RF absorber is arranged close to irradiation area for measuring the temperature which is transmitted to the controller. Several needles/probes are implanted at the target location of patient's body.

11 Claims, 4 Drawing Sheets

SYSTEM AND METHOD FOR GENERATING HEAT AT TARGET AREA OF PATIENT'S BODY

CROSS-REFERENCE TO RELATED APPLICATIONS

The present application claims the benefit and the priority of the U.S. Provisional Patent of Application with Ser. No. 61/908,862 filed on Nov. 26, 2013 and the contents of which are incorporated by reference herein.

BACKGROUND

1. Technical Field

The embodiments herein generally relates to the medical systems and methods. The embodiments herein particularly relates to the treatment of lesions, tumors, cancer cells, body pain and nerve pain. The embodiments herein more particularly relates to a method and system for generating heat at a target area in a patient's body to treat the lesions, tumors, cancer cells, body pain and nerve pain.

2. Description of the Related Art

Heat has been used to manage pain since ancient days. In modern pain management, among other modalities, heat is used to cure lesions and to burn or change the behavior of nerves. Radio frequency therapy and other ablative procedures are typically adapted to treat various chronic pain cases. The radio frequency waves are employed to generate heat at the tip of a needle or probe and the heat generated is utilized to destroy a target. The target can be a nerve or an invasive tumor and a variety of growths. The process for generating heat using radio frequency waves involves steps of: detecting the target area using an imaging technique such as X-rays, MRI scans, ultrasound, other imaging modalities and surface landmarks; inserting the needle or probe through the skin and guiding the needle or probe to the target using imaging techniques and surface landmarks. Using radiofrequency waves or direct heat, the nerve or the target structure is burnt and destroyed. Further enough heat is generated to calm and cease pain. However nerves do grow back and typically the procedure needs to be repeated in six months to a year. This is due to the fact that the nerves that are ablated do grow back and in most cases, the pain of the patient returns. In the view of the foregoing, there is a need for a treatment method for repeatedly providing heat to the target are at short or long term intervals.

In order to access the target, the physician needs to insert a needle or probe through the skin at each session. The needle has to go through many layers of tissue including skin, connective tissue and muscles. This increases the chance for complications including infections and bleeding. The needle itself causes pain as well. The ultimate position of the needle also varies to some degree at each procedure. Hence there is a need for eliminating the need for inserting the needles and probes into the body of the patient at periodic intervals such as every few months and reducing a pain of the patient and discomfort from the repeated insertion of the needles. Also, there is a need for a treatment method that reduces the risks of infection and bleeding and reduces cost.

The above mentioned shortcomings, disadvantages and problems are addressed herein and which will be understood by reading and studying the following specification.

OBJECTS OF THE EMBODIMENTS

The primary object of the embodiments herein is to provide a system and method for generating heat at a target area of a body of a patient to treat the lesions, tumors, cancer cells, body pain and nerve pain.

Another object of the embodiments herein is to provide a treatment method for repeatedly generating heat to the target area at short or long intervals of time.

Yet another object of the embodiments herein is to provide a temperature monitor and control system for remotely observing and notifying a temperature condition at the target area.

Yet another object of the embodiments herein is to provide a tissue friendly apparatus manufactured from the metals/alloys/Composite material that maximize a heat generation.

Yet another object of the embodiments herein is to implant the needles/probes at the target location of patient's body in-order to eliminate a need to insert the needle/probe on multiple occasions.

These and other objects and advantages of the present invention will become readily apparent from the following detailed description taken in conjunction with the accompanying drawings.

SUMMARY

The various embodiments herein provide a method and system generating heat at a target area of a patient's body. The system for generating heat at a target area of a patient's body comprises a radio frequency (RF) generator for generating radio frequency (RF) waves and a radio frequency (RF) antenna or transducer for receiving the generated radio frequency (RF) waves from the radio frequency (RF) generator. A controller or optimizer is provided for controlling a frequency of the radio frequency (RF) waves and a transmission timing which comprises a start time and a stop time of the transmission of the radio frequency (RF) waves. A radio frequency (RF) absorber or distributor comprising a plurality of closed loop circuits is provided. A miniaturized thermometer is arranged for measuring the temperature and transmitting the measured temperature to a wireless transmitter. The wireless transmitter further transmits the measured temperature to a wireless receiver.

According to one embodiment herein, the miniaturized thermometer is positioned inside the radio frequency absorber or distributor. The miniaturized thermometer is positioned close to the nerve or the disk to be irradiated.

According to one embodiment herein, the radio frequency (RF) antenna or transducer, the controller or optimizer and the wireless receiver collectively form an external part of the system.

According to one embodiment herein, the miniaturized thermometer, the radio frequency (RF) absorber or distributor and the wireless transmitter collectively form an internal part of the system.

According to one embodiment herein, the miniaturized thermometer, the radio frequency (RF) absorber or distributor and the wireless transmitter are placed in a screw. The screw is made of metals with a high radio frequency (RF) absorption characteristics or coefficient. The radio frequency (RF) absorber or distributor is made of metal or silicon based material whose rate of absorbing radio frequency (RF) is higher than that of biological tissues.

According to one embodiment herein, the wireless transmitter is configured to transmit the measured temperature with the miniaturized thermometer to the wireless receiver. The wireless receiver is placed outside the body of the patient.

According to one embodiment herein, the wireless receiver is configured to transmit the received temperature information to the controller or optimizer.

According to one embodiment herein, the controller or optimizer calculates a preferred value for RF energy, RF frequency, start and stop time for the treatment, and wherein the values are calculated based on the received temperature information.

According to one embodiment herein, the controller or optimizer is selected from the group consisting of a Proportional-Integral-Derivative (PID) controller, an Optimal Controller, a Fuzzy Controller, a Neural Controller and a Model-Based Controller.

According to one embodiment herein, the controller or optimizer is further configured to maintain the level of measured temperature inside the tissue at a desired level during the course of treatment.

According to one embodiment herein, the radio frequency (RF) antenna or transducer is configured to receive the RF energy value, RF frequency value, and start and stop time for the treatment. The radio frequency (RF) generator is configured to irradiate the RF energy towards the nerve or disk and the radio frequency (RF) absorber or distributor.

According to one embodiment herein, the radio frequency (RF) absorber or distributor provides for a re-circulation of radio frequency (RF) energy. The radio frequency (RF) absorber or distributor is configured to generate heat from the magnetic energy of radio frequency (RF). The radio frequency (RF) absorber or distributor is further configured to distribute the generated heat to the nerve or the disk.

According to one embodiment herein, the screws or the absorbers or the distributors convert the magnetic energy to heat inside the tissue and transfer the heat to disks and nerves.

The various embodiments herein provide a method for generating heat at a target area of a patient's body. The method comprises the steps of identifying a target area in a patient's body for radio-frequency ablation. On locating the target area, one or more wires or probes or plates or rods are inserted and implanted at the target area of the patient's body. Further the amount of radio frequency (RF) energy required to achieve the desired temperature at the target site is calculated. The patient is placed in a magnetic field of the generated RF waves. The heat is generated around the target area of the patient's body utilizing the radio frequency (RF) waves. The heat generated destroys the target remotely.

According to one embodiment herein, the temperature at the target area is monitored remotely and the monitored temperature information is sent to the physician at regular interval of time.

According to one embodiment herein, the identification of the target area in the patient's body for radiofrequency ablation is done through one or more imaging studies selected from the group consisting of X-rays, CT scans, MRIs, and physical examination of the patient, response to previous treatment modalities, and diagnostic local anesthetic injections, and wherein the probe is inserted when the target is identified.

According to one embodiment herein, the wire type probes are inserted percutaneously using a needle under the guidance of fluoroscopy or CT scan.

According to one embodiment herein, the larger probes and rods are inserted surgically under direct vision and secured at the target location in the patient's body.

According to one embodiment herein, the method for generating heat at the target area of the patient's body further comprises the steps of calculating the amount of radio frequency energy required to achieve the desired temperature at the target site. The steps involves an estimation of values of at-least last two measured temperatures at time "t−1" and "t". One or more fuzzy rules are applied on the estimated temperature values at time "t−1" and "t". The power of the radio frequency (RF) is identified based on the fuzzy rules and the temperature values. Further the frequency and timing of radio frequency (RF) is identified based on the measured temperature.

According to one embodiment herein, the method provides a real time monitoring of the generated heat and the temperature of the tissue.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

Figure 1:
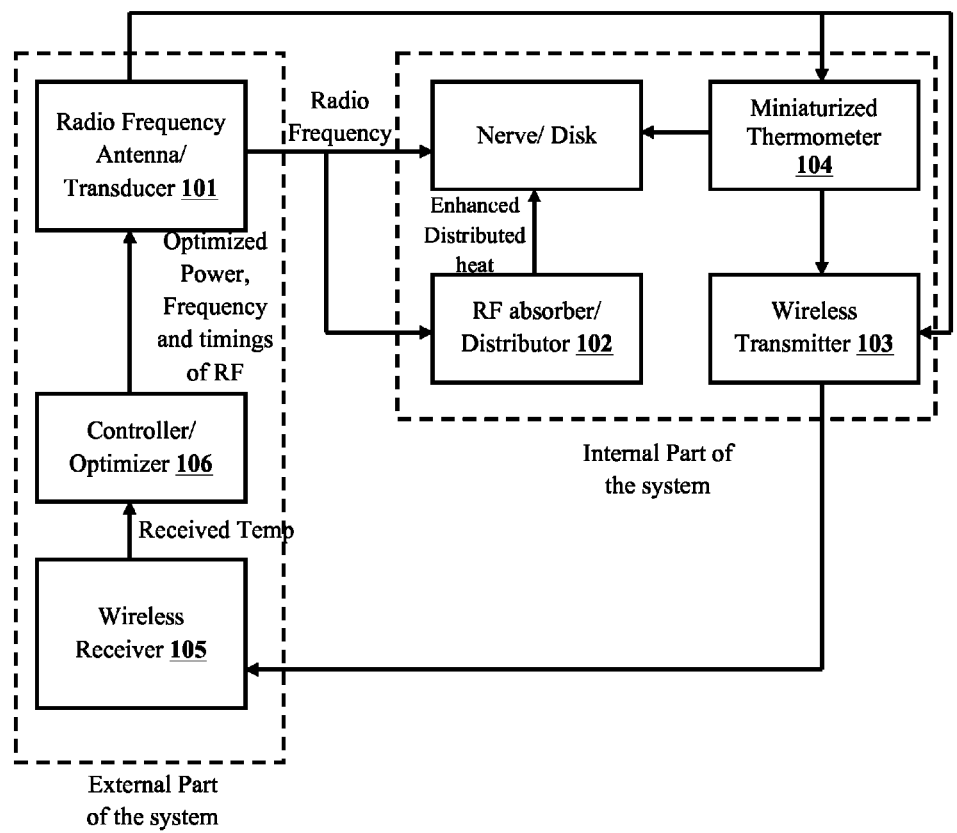
FIG. 1 illustrates a block diagram of the system for generating heat at the target area of the patient's body, according to an embodiment herein.

The various embodiments herein provide a method and system for generating heat at a target area of a patient's body. The system uses radio frequency radiation to generate heat inside a tissue of the target and the heat generated is distributed throughout the target area. FIG. 1 illustrates a block diagram of a system that generates heat at the target area of the patient's body, according to an embodiment herein. The system comprises an internal part/unit/section and an external part/unit/section. The system comprises a plurality of needles/probes/plates/rods, a radio frequency (RF) antenna/transducer 101, a radio frequency (RF) generator, a controller/optimizer 106, a wireless receiver 105, a radio frequency (RF) absorber/distributor 102, a miniaturized thermometer 104, and a wireless transmitter 103. The miniaturized thermometer 104, the radio frequency (RF) absorber/distributor 102, the wireless transmitter 103 and the plurality of needles/probes collectively or integrally form an internal part/unit of the system. The radio frequency (RF) antenna/transducer 101, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes/plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the needle or probe. The target area for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the miniaturized thermometer 104 of the system is configured to measure a temperature of a nerve or disk at the target place. The miniaturized thermometer 104 is positioned inside the RF absorber/distributor 102, and the absorber/distributor 102 is placed close to the nerve or disk to be irradiated. The information corresponding to the measured temperature is transmitted over the wireless transmitter 103 to the external part of the system. The miniaturized thermometer 104 operates on a radio frequency (RF) charged battery. The battery uses the RF energy emitted by the RF transducer to recharge itself.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-Integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, start and stop time for the treatment and accordingly irradiates the RF radiation. The radio frequency (RF) antenna/transducer 101, in communication with the RF generator, irradiate the RF radiations towards the nerve/disk and the radio frequency (RF) absorber/distributor 102.

Figure 2A:
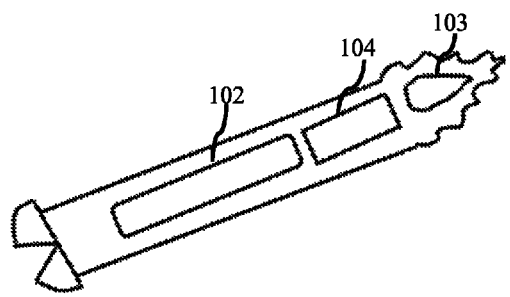
FIG. 2A illustrates a plan view of a screw with a closed loop circuit for heat generators for generating heat from the magnetic field of the RF radiations in the system for generating heat at the target area of the patient's body, according to an embodiment herein.

FIG. 2A illustrates a structural diagram of a screw used to generate heat from the magnetic field of the RF radiations, according to an embodiment of the present disclosure. The miniaturized thermometer 104, the radio frequency (RF) absorber/distributor 102 and the wireless transmitter 103 are placed in the screw. The screw is made of metals or Composite having a high rate of radio frequency (RF) absorbability. The radio frequency (RF) absorber/distributor, in communication with the RF antenna/transducer, is configured to convert the magnetic energy of the RF radiations to heat, inside the tissue of the target area and transfer the heat to the disks and/or nerves or other structures.

Figure 2B:
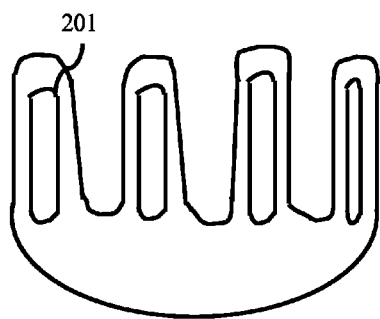
FIG. 2B illustrates a top view of a RF absorber/transducer with a closed loop circuit for electron flow in the system for generating heat at the target area of the patient's body, according to an embodiment herein.
Figure 2C:
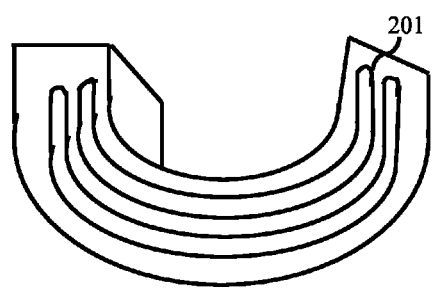
FIG. 2C illustrates a top view of a RF absorber/transducer with a multilayer structure comprising multiple closed loop circuits for generating heat in the system for generating heat at the target area of the patient's body, according to an embodiment herein.

FIG. 2B and FIG. 2C illustrates a structural diagram of a RF absorber/distributor 102 that comprises a plurality of closed loop circuits 201, according to an embodiment of the present disclosure. The plurality of closed loop circuits 201 is configured to perform re-circulation of electrons and to amplify the process of conversion of RF energy to heat. The RF absorbers/distributors 102 are made of a metal and/or silicon or composite based material whose rate of absorbing RF is higher than biological tissues. The system is designed to be independent of the material used as distributor/absorber/screws, which enables the system to work with all types of implantable material.

Figure 3:
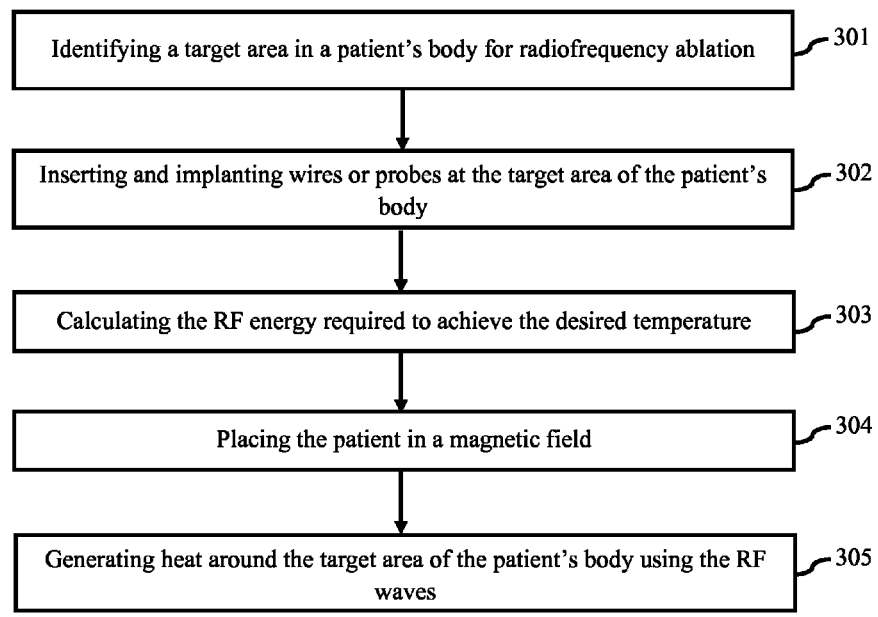
FIG. 3 illustrates a flowchart explaining the process steps in the method for generating heat at a target area of a patient's body, according to an embodiment herein.

The various embodiments herein provide a method for generating heat at a target area of a patient's body. FIG. 3 illustrates a flowchart indicating the steps involved in the method for generating heat at a target area of a patient's body, according to an embodiment of the present disclosure. The method comprises following steps of: A target area is identified in a patient's body for radio-frequency ablation (301). One or more wires or probes or plates or rods are inserted and implanted at the target area of the patient's body (302). The amount of radio frequency (RF) energy required to achieve the desired temperature at the target site is calculated (303). The patient is placed in a magnetic field (304). The heat is generated at the target area of the patient's body utilizing the radio frequency (RF) waves (305). The heat generated destroys the target remotely. The temperature at the target area is monitored remotely, and the monitored temperature information is sent to the physician at regular interval of time.

According to one embodiment herein, the steps for calculating the amount of radio frequency energy required to achieve the desired temperature at the target site comprises: The values of at-least last two measured temperatures are estimated at time "t−1" and "t". One or more fuzzy rules are applied on the estimated temperature values at time "t−1" and "t". The power of the radio frequency (RF) is identified based on the fuzzy rules and the temperature values. Further the frequency and timing of radio frequency (RF) radiation is identified based on the measured temperature.

According to one embodiment of the present invention, the formulation used by the system for calculating the parameters required to achieve the desired temperature at the target site comprises a sensor/controller mechanism that is implemented with highly intuitive systems such as fuzzy controller.

Table 1 depicts an example of the fuzzy rules that are defined directly by physicians. The fuzzy rules are further optimized by fuzzy algorithms.

TABLE 1

An example for the fuzzy rules that are defined directly by physicians

| Temp at time t | Temp at time t − 1 | | | | |
|---|---|---|---|---|---|
| | Very Low | Low | Med | High | Very High |
| Very Low | Increase RF Much | Increase RF Much | Maintain RF Level | Decrease RF Some | Decrease RF Much |
| Low | Increase RF Much | Increase RF Much | Maintain RF Level | Maintain RF Level | Decrease RF Some |
| Med | Maintain RF Level | Maintain RF Level | Maintain RF Level | Maintain RF Level | Decrease RF Much |
| High | Maintain RF Level | Maintain RF Level | Maintain RF Level | Decrease RF Some | Decrease RF Much |
| Very High | Decrease RF Some | Decrease RF Some | Decrease RF Some | Decrease RF Much | Decrease RF Much |

Figure 4:
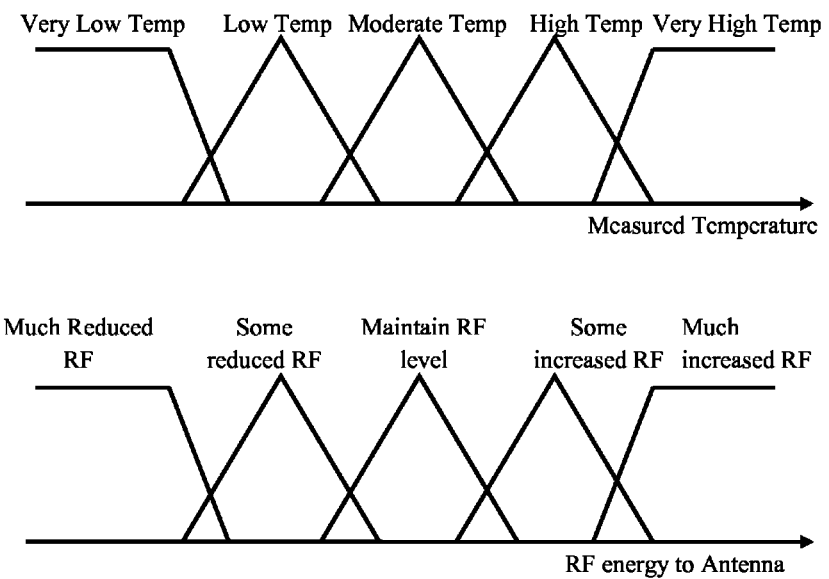
FIG. 4 illustrates a timing chart for the fuzzy sets defining the plurality of fuzzy variables/identifiers, in the method for generating heat at a target area of a patient's body, according to an embodiment herein.

As shown in Table 1, based on the values of the last two measured temperatures (at times "t−1" and "t"), simple fuzzy rules are used to identify the power of the RF. FIG. 4 illustrates fuzzy sets defining various fuzzy variables/identifiers, according to an embodiment of the present disclosure. As shown in FIG. 4, all input and output variables for the controller (in this case temperature and RF energy, respectively) are defined using identifiers such as very low, low, medium, high, very high, and the like. The range of each of these identifiers is initialized and adjusted by the physician. In FIG. 4, triangular membership function is employed to create fuzzy sets but other functions such as trapezoidal and Gaussian are also used for the purpose as well. The physician supervises the controller and easily adjust/revise the function of the controller by changing the values in Table 1 and/or membership functions/sets in FIG. 4. The same type of controller identifies the frequency and timing of RF based on measured temperature.

The foregoing description of the specific embodiments herein will so fully reveal the general nature of the embodiments herein that others can, by applying current knowledge, readily modify and/or adapt for various applications such specific embodiments herein without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments herein with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A system for generating heat at a target area of a patient's body comprising: a radio frequency (RF) antenna or transducer; a radio frequency (RF) generator for generating radio frequency (RF) waves, and wherein the radio frequency (RF) generator transmits the generated radio frequency (RF) waves to the radio frequency (RF) antenna or transducer; a controller or optimizer for controlling frequency of the radio frequency (RF) waves to be transmitted by the radio frequency (RF) antenna or transducer and a transmission timing, and wherein the transmission timing comprises a start time and a stop time of the transmission of the radio frequency (RF) waves; a radio frequency (RF) absorber or distributor, wherein the radio frequency (RF) absorber comprises a plurality of closed loop circuits; and a miniaturized thermometer, wherein the miniaturized thermometer is positioned inside the radio frequency absorber or distributer, and wherein the miniaturized thermometer is adapted to be positioned close to the target area of the patient's body, and wherein the miniaturized thermometer measures the temperature and transmit the measured temperature to a wireless transmitter, and wherein the wireless transmitter transmits the measured temperature to a wireless receiver.

2. The system according to claim 1, wherein the radio frequency (RF) antenna or transducer, the controller or optimizer and the wireless receiver collectively form an external part of the system.

3. The system according to claim 1, wherein the miniaturized thermometer, the radio frequency (RF) absorber or distributor and the wireless transmitter collectively form an internal part of the system, and wherein the miniaturized thermometer, the radio frequency (RF) absorber or distributor and the wireless transmitter are placed in a screw, and wherein the radio frequency (RF) absorber or distributor is made of metal or silicon based material whose rate of absorbing radio frequency (RF) is higher than biological tissues.

4. The system according to claim 1, wherein the wireless transmitter is configured to transmit measured temperature received from the miniaturized thermometer to the wireless receiver, and wherein the wireless receiver is placed outside the patient's body.

5. The system according to claim 1, wherein the wireless receiver is configured to transmit the received temperature information to the controller or optimizer.

6. The system according to claim 1, wherein the controller or optimizer calculates a preferred value for RF energy, RF frequency, start and stop time for the treatment, and wherein the values are calculated based on the received temperature information.

7. The system according to claim 1, wherein the controller or optimizer is any of a controller or optimizer selected from the group consisting of a Proportional-Integral-Derivative (PID) controller, an Optimal Controller, a Fuzzy Controller, a Neural Controller and a Model-Based Controller.

8. The system according to claim 1, wherein the controller or optimizer is further configured to maintain the level of measured temperature inside the tissue at a desired level during a course of treatment.

9. The system according to claim 1, wherein the radio frequency (RF) antenna or transducer is configured to receive the value for RF energy, RF frequency, and start and stop time for the treatment, and wherein the radio frequency (RF) generator is configured to irradiate RF energy towards the nerve or disk and the radio frequency (RF) absorber or distributor.

10. The system according to claim 1, wherein the radio frequency (RF) absorber or distributor provides re-circulation of radio frequency (RF) energy, and wherein the radio frequency (RF) absorber or distributor is configured to generate heat from magnetic energy of radio frequency (RF), and wherein the radio frequency (RF) absorber or distributor is further configured to distribute generated heat to the nerve or the disk.

11. The system according to claim 1, wherein the screws or the absorbers or the distributors converts the magnetic energy to heat inside the tissue and transfer the heat to disks and nerves.

* * * * *